US008940705B2

(12) United States Patent
Diamond et al.

(10) Patent No.: US 8,940,705 B2
(45) Date of Patent: Jan. 27, 2015

(54) METHOD OF TREATING DISEASE AND SELECTIVELY MODULATING TRANSCRIPTIONAL REGULATION BY A GLUCOCORTICOID RECEPTOR BY ADMINISTERING ACLACINOMYCIN AND DEXAMETHASONE

(75) Inventors: Marc Diamond, Clayton, MO (US); Anthony Gerber, Denver, CO (US)

(73) Assignee: The Regents of the University of California, Oakland, CA (US)

( * ) Notice: Subject to any disclaimer, the term of this patent is extended or adjusted under 35 U.S.C. 154(b) by 218 days.

(21) Appl. No.: 13/143,727

(22) PCT Filed: Jan. 8, 2010

(86) PCT No.: PCT/US2010/020517
§ 371 (c)(1),
(2), (4) Date: Nov. 23, 2011

(87) PCT Pub. No.: WO2010/081015
PCT Pub. Date: Jul. 15, 2010

(65) Prior Publication Data
US 2012/0094945 A1    Apr. 19, 2012

Related U.S. Application Data

(60) Provisional application No. 61/143,730, filed on Jan. 9, 2009.

(51) Int. Cl.
*A61K 31/573* (2006.01)
*A61K 31/704* (2006.01)
*A61K 31/57* (2006.01)
*A61K 9/00* (2006.01)

(52) U.S. Cl.
CPC ............. *A61K 31/573* (2013.01); *A61K 31/704* (2013.01); *A61K 31/57* (2013.01); *A61K 9/0014* (2013.01); *A61K 9/0019* (2013.01); *A61K 9/0053* (2013.01)
USPC ......................................................... 514/27

(58) Field of Classification Search
None
See application file for complete search history.

(56) References Cited

U.S. PATENT DOCUMENTS

2006/0183674 A1    8/2006    Brand et al.

FOREIGN PATENT DOCUMENTS

| EP | 0234897 A2 * | 2/1987 | ............. A61K 31/57 |
| EP | 1261337 B1 * | 9/2008 | ......... A61K 31/4439 |
| WO | WO 2008027988 A2 * | 3/2008 | ........... A61K 31/192 |

OTHER PUBLICATIONS

Wilkinson, Pharacokinetics. In Goodman and Gilman's The Pharmacological Basis of Theraputics. Ed. Hardman. McGraw-Hill, New York. 2001.*
Croxtall, J. D., Van Hal, P. T. W., Choudhury, Q., Gilroy, D. W., & Flower, R. J. (2002). Different glucocorticoids vary in their genomic and non-genomic mechanism of action in A549 cells. British journal of pharmacology, 135(2), 511-519.*
International Search Report and Written Opinion dated Mar. 9, 2010, issued in related International Patent Application No. PCT/US2010/020517, filed Jan. 8, 2010.
Alheim et al., "Bisanthracycline WP631 inhibits basal and Sp1-activated transcription initiation in vitro," 1999, Nucleic Acids Res., 27: 3402-3409.
Liu et al., Glucocorticoids activate somatostatin gene transcription through co-operative interaction with the cyclic AMP signalling pathway.
Martin et al., "Bisanthracycline WP631 inhibits basal and Sp1-activated transcription initiation in vitro," 1999, Nucleic Acids Res., 27: 3402-3409.
Matsuzawa et al., "Structure-activity relationships of anthracyclines relative to cytotoxicity and effects on macromolecular synthesis in L1210 leukemia cells," 1981, J. Antibiot. (Tokyo), 34(2): 1596-1607.
Thompson et al., "Glucocorticoids, oxysterols, and cAMP with glucocorticoids each cause apoptosis of CEM cells and suppress c-myc," 1999, J. Steroid Biochem Mol. Biol. 69(1-6): 453-461.
Wu et al., "Regulatory perspectives of Type II prodrug development and time-dependant toxicity management: Nonclinical Pharm/Tox analysisi and the role of comparative toxicology," 2007, Toxicology, 236: 1-6.

* cited by examiner

*Primary Examiner* — Scarlett Goon
*Assistant Examiner* — Dale R Miller
(74) *Attorney, Agent, or Firm* — Kilpatrick Townsend & Stockton LLP

(57) ABSTRACT

The invention relates to assays to detect selective gene regulation by ligand dependent transcription factors. The invention also relates to selective modulators of the glucocortocoid receptor for treatment of inflammation and allergic and immune-mediated diseases.

7 Claims, 9 Drawing Sheets

METHOD OF TREATING DISEASE AND SELECTIVELY MODULATING TRANSCRIPTIONAL REGULATION BY A GLUCOCORTICOID RECEPTOR BY ADMINISTERING ACLACINOMYCIN AND DEXAMETHASONE

CROSS-REFERENCES TO RELATED APPLICATIONS

This application is the U.S. National Stage entry of International Application No. PCT/US2010/020517, filed Jan. 8, 2010, which claims priority to U.S. Provisional Patent Application No. 61/143,730, filed Jan. 9, 2009, which are incorporated in their entirety herein for all purposes.

STATEMENT AS TO RIGHTS TO INVENTIONS MADE UNDER FEDERALLY SPONSORED RESEARCH AND DEVELOPMENT

This invention was made with government support under grant no. K08 HL077159 awarded by the National Institutes of Health. The government has certain rights in the invention.

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

GR is a nuclear receptor (NR), a family of intracellular ligand-regulated transcription factors (McMaster, A. et al., *Exp Physiol* 92:299-309 (2007)). GR is expressed ubiquitously in humans. Activation of GR by hormones such as cortisol causes nuclear translocation, interaction with co-regulators, and binding to specific genomic sites to regulate transcription (Yamamoto, K. R. et al., *Cold Spring Harbor Symposia on Quantitative Biology* 63:587-598 (1998); So, A. Y. et al., *PLoS Genet* 3:e94 (2007)). This mediates the broad systemic effects of GR signaling and underlies glucocorticoid treatment of diverse immune-mediated diseases such as asthma and rheumatoid arthritis. However, severe dose-limiting side effects occur, including osteoporosis, muscle wasting, and diabetes (Schacke, H. et al., *Pharmacology & Therapeutics* 96:23-43 (2002)). No existing drugs selectively induce beneficial effects of GR.

Beneficial and harmful effects of glucocorticoids are due to selective activation or repression of particular genes by GR. This selectivity is in part based on tissue-specific factors and cross-talk pathways (Kassel, O. et al., *Molecular and Cellular Endocrinology* 275:13-29 (2007)). For example, GR reduces the expression of certain inflammatory cytokines by inhibiting other transcription factors such as AP-1 and NF-Kb (Smoak, K. A. et al., *Mech Ageing Dev* 125:697-706 (2004)). Conversely, GR increases expression of RANKL, a gene co-regulated by the Vitamin D receptor that activates bone resorption by osteoclasts (Hofbauer, L. C. et al., *Endocrinology* 140:4382-4389 (1999); Kim, S. et al., *Mol. Cell. Biol.* 26:6469-6486 (2006)). Controlling GR activity at certain tissues or promoters has profound therapeutic implications.

Efforts to achieve this goal have focused primarily on developing selective GR ligands that simply induce a subset of GR activities (Rosen, J. et al., *Endocr Rev* 26:452-464 (2005); Cole, T. J. et al., *Medicinal Chemistry* 3:494-506 (2007); Honer, C. et al., *Mol Pharmacol* 63:1012-1020 (2003)); see also assays described in U.S. Pat. No. 5,968,738 and WO/2001/516077. However, it is not yet possible to predict GR gene regulation based on ligand design, and it remains uncertain whether new ligands can produce therapeutically relevant transcriptional selectivity. Moreover, transcription based screens for novel GR modulators generally measure GR activation at a single experimental promoter (Fan, F. et al., *ASSAY and Drug Development Technologies* 5:127-136 (2007)). This does not allow efficient identification of molecules that produce promoter-specific responses. Accordingly, although numerous GR agonists with different potencies and/or modes of delivery are in clinical use, dose equivalency generally results in similar clinical responses and side effects (Adams, N. et al., *Cochrane Database Syst Rev*, CD002310 (2007)). Non-ligand modulation of GR is an alternative strategy to achieve the desired transcriptional output, potentially enabling tissue or promoter-specific GR effects.

To address this problem, we developed a high throughput system to measure GR activity at four promoters. This permits discovery of genes or molecules that alter GR signaling in a promoter-specific fashion. We have applied this system to identify selective GR modulators in an initial screen of 1040 natural products and FDA-approved compounds.

In addition, the assay disclosed herein can be applied to detect selective gene regulation by ligand dependent transcription factors such as nuclear receptors, by assaying up to five different receptors in a single well. The assay can be used to detect general modulators, cell specific modulators (e.g., a drug that blocks a promoter in one cell type but not another, or protein specific modulators (e.g., a drug that causes a single protein to turn on only a subset of genes that it would ordinarily activate). The assay can help speed the identification of novel ligands or compounds that work through non-receptor binding sites (i.e., cross talk pathways). For example, this assay could be used to identify modulators of glucocorticoid signaling that would cause the receptor to activate immunosuppression genes while avoiding induction of genes that cause muscle wasting.

Additional potential targets include the androgen receptor, which is responsible for initiation and progression of prostate cancer, hirsutism, and mediates muscle hypertrophy in response to anabolic steroids; the estrogen receptor, which is a key target for breast cancer, heart disease, and the female reproductive tract; the thyroid hormone receptor, which plays a key role in regulating metabolism and bone loss; and the mineralocorticoid receptor, which regulates salt metabolism. The general class of nuclear receptors includes the retinoic acid receptor, RXR, the liver X receptor, and peroxisome proliferator activated receptor (PPAR), which plays a key role in fat metabolism. All mediate their effects via selective regulation of gene expression, and have similar modes of action, and thus could be used in this system.

BRIEF SUMMARY OF THE INVENTION

Glucocorticoids are widely used to suppress inflammation and treat various allergic and immune-mediated diseases. Some glucocorticoid receptor (GR) regulated genes mediate the therapeutic response, while others cause debilitating side effects. To discover selective modulators of GR, we developed a high throughput, multiplexed system to monitor GR regulation of four promoters simultaneously. An initial screen of 1040 natural products and FDA-approved compounds identified selective modulators of GR signaling. We discovered a non-steroidal agonist, several antagonists, and selective modulators that caused GR to activate only a subset of three target promoters. This approach will facilitate identification of genes and small molecules that augment beneficial effects of GR, while diminishing deleterious ones. Our results have important implications for developing novel GR modulators and identifying cross-talk pathways that control selective GR gene regulation. Although we have here used a limited set of promoters, this assay can be adapted to any promoter of interest that is regulated by GR, or any other nuclear receptor, transcription factor, or signaling pathway that impacts gene expression.

A-B. Fluorescence microscopy of A549 cells transfected with pFKBP5-OFP and treated with dex as indicated.

C. The peak fluorescent output of A549 cells transfected with the indicated reporter constructs and treated with dex as indicated was measured using a monochrometer-based plate reader.

D. Cells were transfected with each FP reporter construct and treated with dex as indicated. The fluorescent output above background was measured sequentially with each of the four optimized excitation/emission pairs. Values above background measured with the optimal setting for each reporter with dex treatment were normalized to 100%. Note that minimal fluorescent signal was detected for each reporter at non-optimal settings.

E. Fluorescent outputs from cells in 96 well dishes transfected with the four fluorescent reporters were sequentially measured using the four excitation/emission pairs.

Mean and standard deviations of raw fluorescent measurements from 8 wells treated with and without dex are graphed as percent activation.

Figure 2:
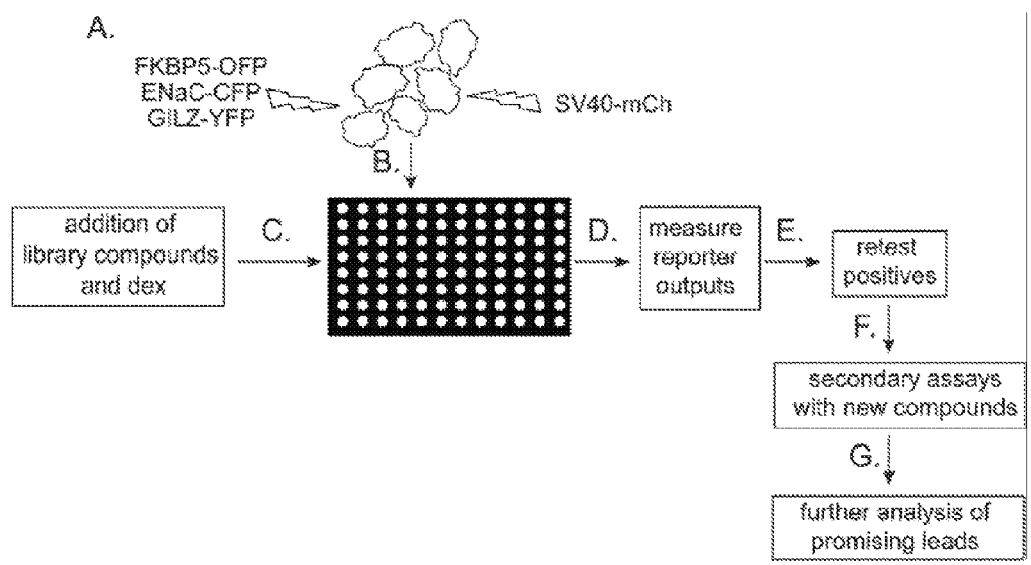

FIG. 2 shows design of multi-promoter based screen for GR modulators.

A. Cells were transfected with the indicated fluorescent protein reporter plasmids.

B. The next day, cells were plated into 96 well dishes.

C. Two hours later, dex (100 nM) and library compounds (2.5 μM) were robotically added to the cells.

D. The next day, fluorescent output for each reporter was measured with a plate reader.

E. Hits were selected based on predefined criteria (see methods) and retested in the screening assay.

F. Fresh compounds of repeat hits were obtained and retested in FP assays and dose response studies.

G. Selected compounds were analyzed in further detail.

Figure 3:
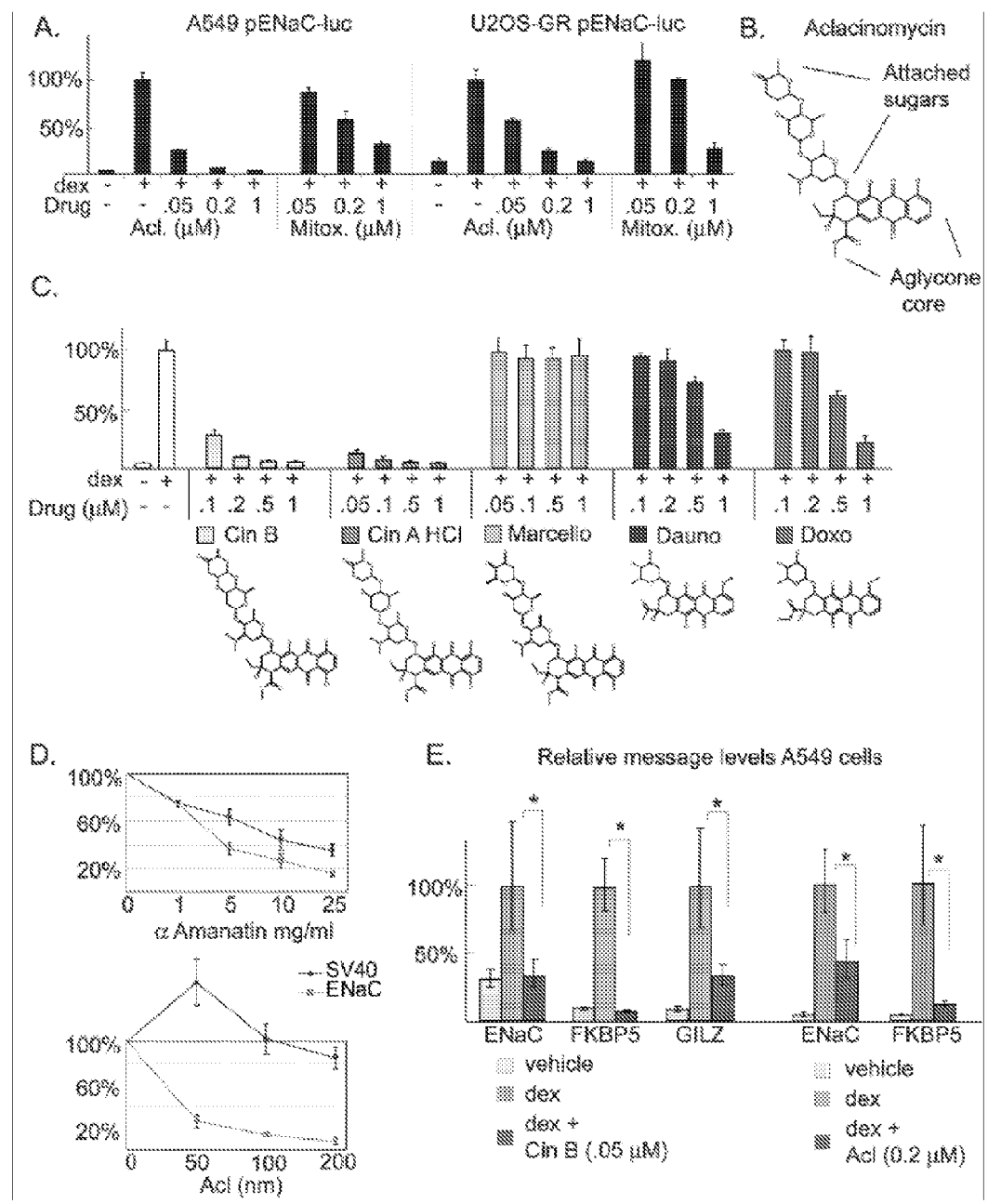

FIG. 3 shows anthracyclines are GR antagonists.

A. Luciferase assays were performed with lysates from A549 and U2OS-GR cells transfected with pENaC-luc and pSV40-rl following treatment with different concentrations of aclacinomycin (Acl.) and mitoxantrone (Mitox.) for 18 hours. Mean and standard deviation of four or more replicates are shown.

B. Structure of aclacinomycin.

C. Luciferase assays were performed with lysates from A549 cells transfected with pENaC-luc and pSV40-rl following treatment with increasing concentrations of drugs as shown for 18 hr. Cin=cinerubin, Marcello=marcellomycin; Doxo=doxorubicin; Dauno=daunorbicin.

D. Luciferase assays were performed on A549 cells transfected with pENaC-luc and pSV40-rl and treated with dex and increasing concentrations of either a amanatin (aAma) or aclacinomycin (Acl). Absolute activities of the dex-responsive pENaC-luc reporter and the dex-unresponsive pSV40-RL reporter with dex treatment alone were each normalized to 100%. Increases in pSV40-luc activity with low doses of Acl were observed consistently.

E. A549 cells were treated for 4 hr (Cin B) and 24 hr (Acl) as indicated. Relative mRNA levels of the indicated genes were determined in triplicate or quadruplicate using qPCR. The mean relative mRNA level for each GR target gene with dex treatment was normalized to equal 100%. Results are shown from a representative experiment; qualitatively similar data were obtained in replicate experiments. * indicates p≤0.05.

Figure 4:
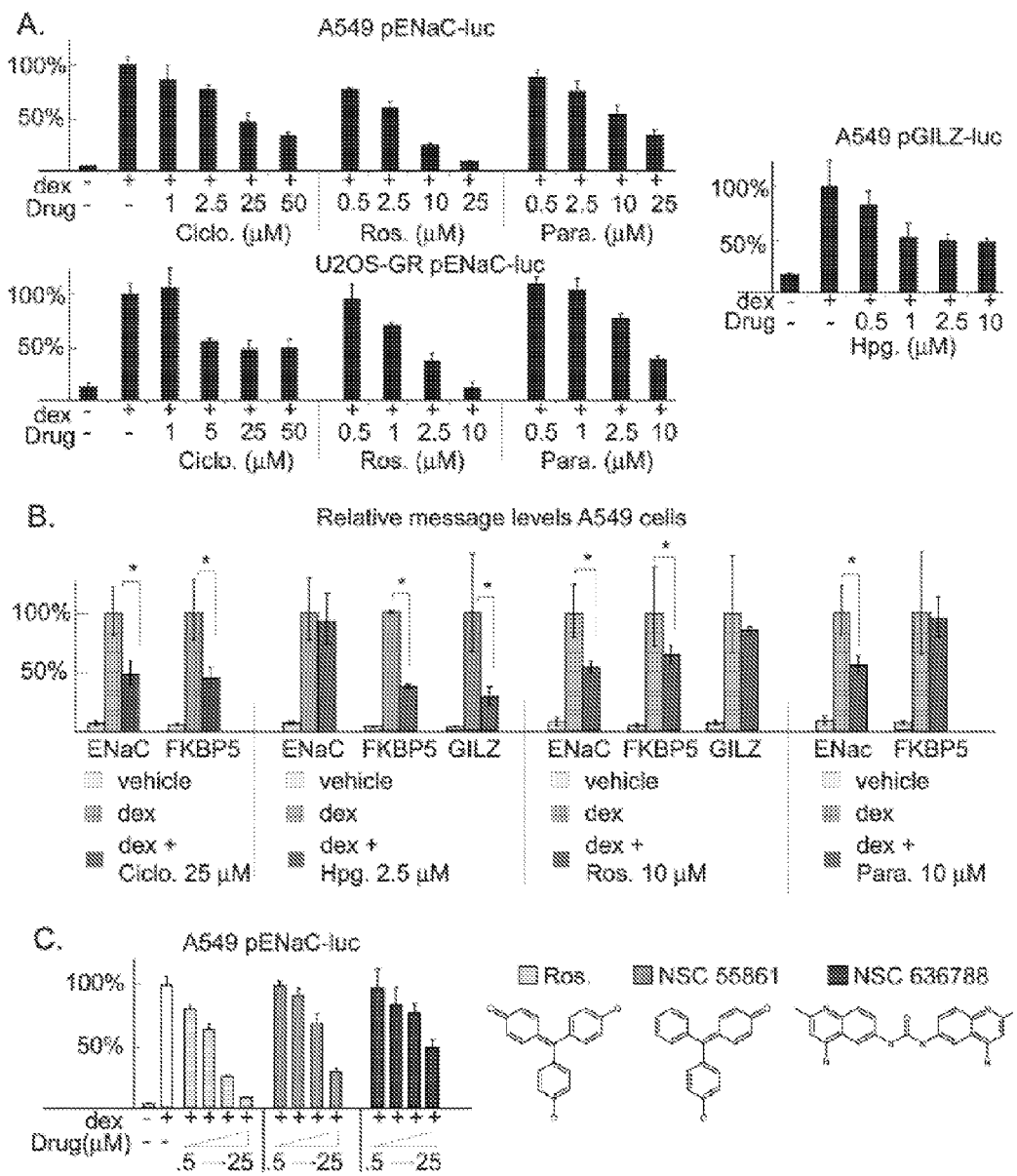

FIG. 4 shows hydroxyprogesterone caproate, rosolic acid, and pararosaniline are selective GR modulators.

A. Luciferase assays were performed on A549 and U2OS-GR cells transfected with pENaC-luc and pSV40-rl and treated with dex and various drugs as indicated. The relative activity of pENaC-luc with dex treatment was normalized to 100%. Ciclo—ciclopirox olamine; Ros—rosolic acid; Para=pararosaniline.

B. Relative mRNA levels of the indicated genes were determined using qPCR.

Cells were treated for 24 hr as indicated. * indicates p≤0.05.

C. Luciferase assays were performed using A549 cells transfected with pENaC-luc and pSV40-rl following treatment with increasing concentrations of drugs (0.5, 2.5, 10 and 25 μM) for 18 hr; the structure of each drug is also shown.

Figure 5:
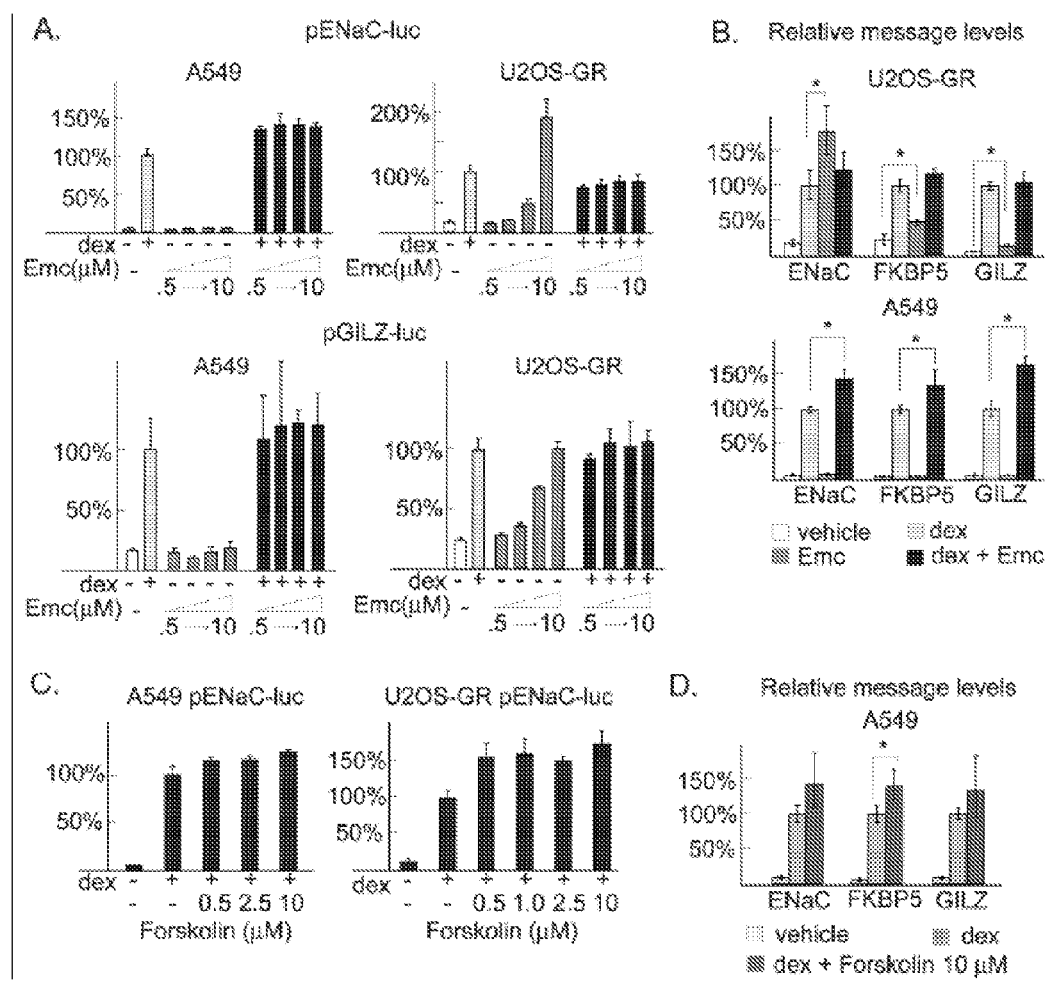

FIG. 5 shows erythromycin cyclopentylpropionate (Emc) and forskolin increase the expression of GR target genes.

A. Luciferase assays were performed using A549 and U2OS-GR cells that were transfected with pENaC-luc and pSV40-rl and treated with dex and Emc (0.5, 1, 2.5 and 10 μM) as indicated. The relative activity of pENaC-luc with dex treatment was normalized to 100%.

B. Relative mRNA levels of the indicated target genes in U2OS-GR and A549 cells were determined using qPCR. Cells were treated for 24 hours as indicated. * indicates p≤0.05.

C. Luciferase assays were performed on A549 and U2OS-GR cells that were transfected with pENaC-luc or PGILZ-luc and pSV40-rl and treated with dex and forskolin as indicated.

D. Relative mRNA levels of the indicated target genes in U2OS-GR and A549 cells were determined using qPCR. Cells were treated for 24 hr as indicated. * indicates p≤0.05.

Figure 6:
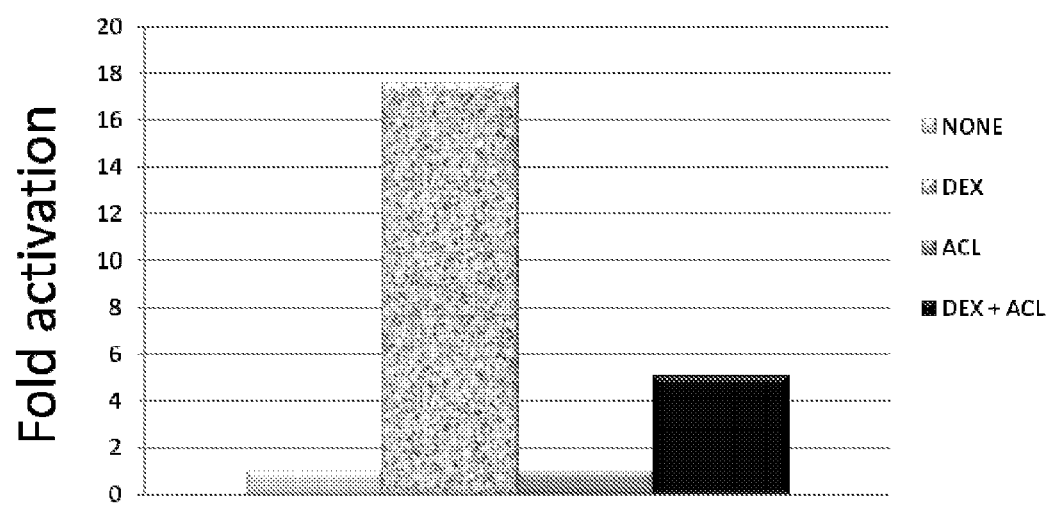

FIG. 6 shows fold activation of FKBP5 in the mouse liver, when treated with placebo, dexamethasone, aclacinomycin and dexamethasone+aclacinomycin.

Figure 7:
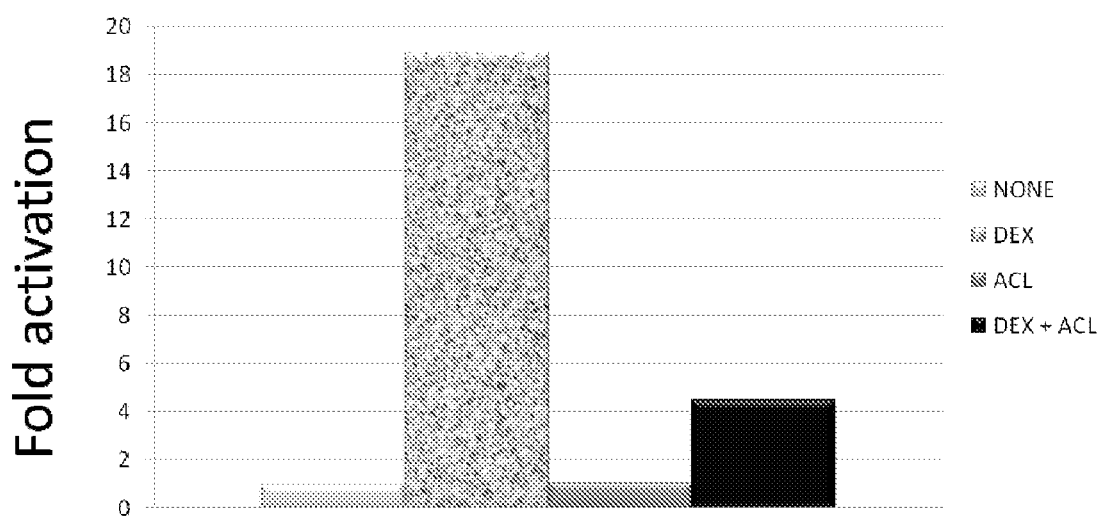

FIG. 7 shows fold activation of FKBP5 in the mouse lung, when treated with placebo, dexamethasone, aclacinomycin and dexamethasone+aclacinomycin.

Figure 8:
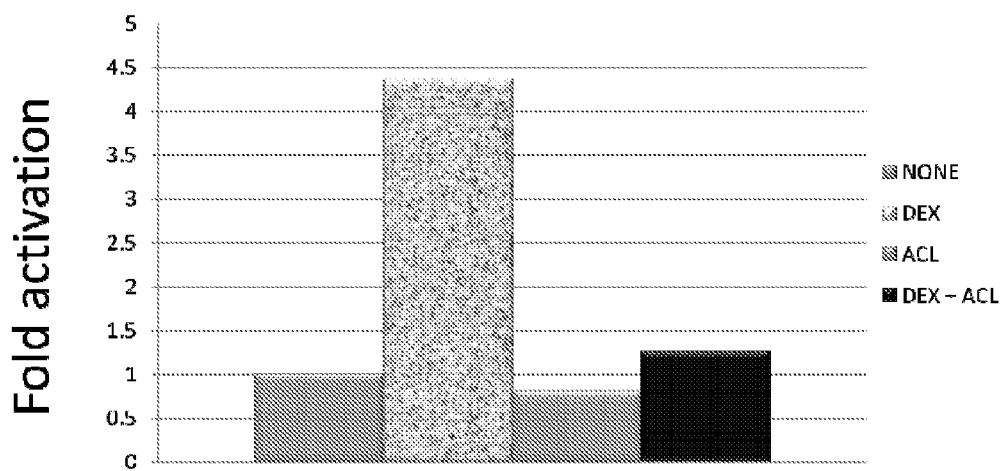

FIG. 8 shows fold activation of KLF15 in the mouse lung, when treated with placebo, dexamethasone, aclacinomycin and dexamethasone+aclacinomycin.

Figure 9:
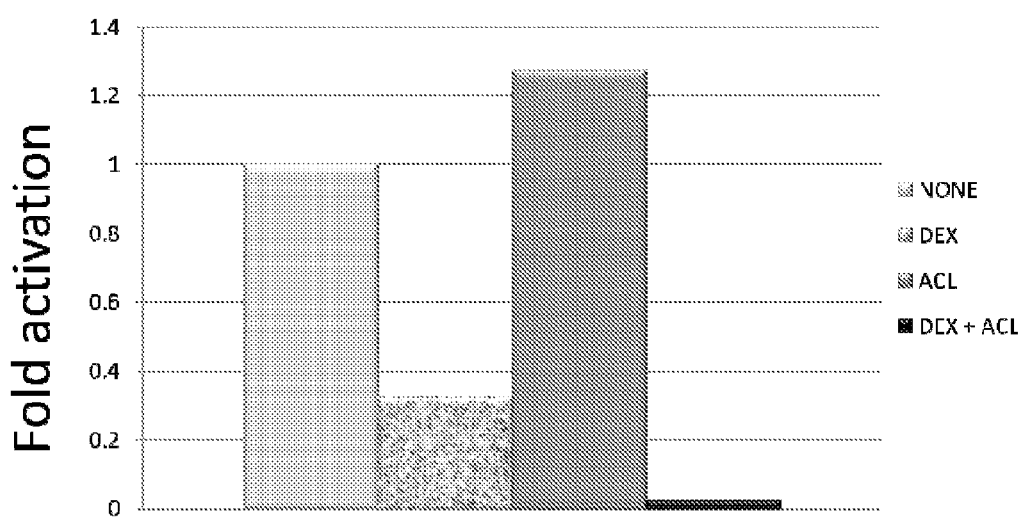

FIG. 9 shows fold activation of CCL2 in the mouse lung, when treated with placebo, dexamethasone, aclacinomycin and dexamethasone+aclacinomycin.

DETAILED DESCRIPTION OF THE INVENTION

I. Introduction

We have developed an assay in which simultaneous measurement of four promoter-fluorescent protein (FP) reporter constructs quantifies promoter activity. In a high-throughput screen of a library of natural products and FDA-approved compounds, we identified multiple classes of compounds that modulate GR signaling at endogenous target genes. Importantly, we discovered several compounds that tuned GR responses, i.e. those that caused GR to regulate only a subset of its normal spectrum of target genes. We also identified molecules that act on GR signaling via heterologous pathways, and a compound with cell specific effects. This work has important implications for drug discovery and for genetic studies to elucidate factors and signaling pathways that regulate GR transcription.

The Power of a Multi-Promoter Readout

Transcriptional regulation is usually measured in high throughput with a single experimental promoter driving an enzyme-based reporter or FP (Necela, B. M. et al., *Steroids* 68:341-350 (2003); Suzuki, T. et al., *Phytomedicine* 13:401-411 (2006); Sonneveld, E. et al., *Toxicol. Sci.* 83:136-148 (2005)). Although laser-based systems and high content microscopy have been proposed as general tools to measure multiple cellular processes, they have not been widely applied for multiplexed measurement of transcription (Auld, D. S. et al., *Methods in Enzymology* (Academic Press, Vol. Volume 414, pp. 566-589 (2006)). The multiplexed GR reporter assay facilitates the identification of compounds (e.g. forskolin) with relatively modest effects on NR signaling. Refinement of weak hits from screening small, biologically active libraries is an attractive alternative to large-scale screens. The system can also be adapted to use mixtures of cell types harboring distinguishable FP-reporters and thereby identify cell-selective modulators such as Emc. At this time, the ease of measurement and low variability of FP expression present advantages over screening systems that directly measure mRNA levels (Hieronymus, H. et al., *Cancer Cell* 10:321-330 (2006)).

Most importantly, the multiplexed system identified compounds that modulated transcription at a subset of promoters from within a group of three targets. For this screen, we selected relatively simple promoters directly activated by GR through distinct GR response elements. However, by varying the promoters to include both beneficial and harmful targets, it should be possible to identify small molecules that tune receptor output to a desired pattern through effects on relevant cross-talk pathways.

In the screen, there were 66 primary hits, of which 14 were steroid-like NR ligands. Six additional hits were validated as non-steroidal GR modulators. Thus, the overall screening efficiency was 30%. However, the percentage of non-steroidal hits that validated as dose-dependent GR regulators was only 11% (6/52). The false positive rate was in part due to edge effects, as the variance of reporter values from plate edges was higher than from plate interiors. Edge effects such as these have been previously described (Lundholt, B. K. et al., *J Biomol Screen* 8:566-70 (2003)), and specific library and plate configurations can reduce variability. It is also possible to reduce false positives by varying the hit criteria and performing screens at more than one drug dose (Wu, Z. et al., *J Biomol Screen* 13:159-67 (2008)).

GR Potentiators

The use of saturating amounts of dex biased the screen to identify GR inhibitors; nevertheless, 7/25 known glucocorticoids within the library were successfully identified. An esterified version of erythromycin, Erythromycin cyclopentylpropionate, was the only novel enhancer of GR signaling identified, and it was discovered through structure activity analysis of a weak hit from the primary screen. We also identified forskolin, previously known to cross-talk with GR by increasing cAMP. Multiplexed screens with sub-saturating levels of dex will likely identify additional compounds that augment GR activity through cross-talk pathways.

Novel Inhibitors of GR

Anthracyclines were identified as novel GR inhibitors. For example, aclacinomycin and cinerubin B, identified via the assay of the present invention, both contain a trisaccharide chain attached to the anthracycline aglycone core that mediates DNA intercalation and is critical for the cytotoxic properties of this drug class (Binaschi, M. et al., *Curr Med Chem Anticancer Agents* 1:113-30 (2001)). Although anthracyclines inhibit the activity of RNA polymerases (Long, B. H. et al., *Mol Pharmacol* 22:152-7 (1982)), the effects we observed cannot be wholly ascribed to non-specific inhibition of transcription (FIG. 3D). Indeed, marcellomycin has a similar $IC_{50}$ for inhibition of RNA synthesis as aclacinomycin (Long, B. H. et al., *Mol Pharmacol* 22:152-7 (1982)) but did not reduce the activation of GR-responsive promoters. We favor a model where intercalation of the anthracycline aglycone core with DNA allows the attached sugars to interact with or displace various DNA-associated factors, including transcription factors, co-factors, and chromatin remodeling complexes, in addition to described effects on RNA Pol II and DNA topoisomerase II (Zunino, F. et al., *Biochemical Pharmacology* 61:933-938 (2001)). This notion is supported by studies finding that several anthracyclines specifically inhibit the activity of transcription factors such as SP-1 (Punchihewa, C. et al., *Mol Cancer Ther* 6:213-219 (2007); Martin, B. et al., *Nucl. Acids Res.* 27:3402-3409 (1999)).

Selective Modulators of GR

Progestins can bind GR and mediate transcriptional effects (Thomas, C. P. et al., *Am J Physiol Renal Physiol* 290:F306-312 (2006)). We identified hydroxyprogesterone caproate (Hpg) as a selective regulator of GR in the primary screen and at endogenous genes. Thus, the multi-promoter assay can be harnessed to identify ligands that specify a desired transcriptional output. Rosolic acid and pararosaniline, which share a common structure of a central carbon bound to three phenyl groups, also selectively modulated GR. As with Hpg, both selectively inhibited promoters in the primary screen, and also selectively antagonized GR activity at endogenous promoters. Pararosaniline was previously reported to inhibit androgen receptor (AR) signaling (Hieronymus, H. et al., *Cancer Cell* 10:321-330 (2006)).

Selective modulation of GR and other nuclear receptors is a major therapeutic goal. Most efforts to achieve selective modulation have been directed at the ligand binding domain of each receptor, which represents only a single facet of the nuclear receptor's activity, and does not directly address receptor interactions with cross-talk pathways (Bai, C. et al., *Assay Drug Dev Technol* 1:843-52 (2003); Kremoser, C. et al., *Drug Discovery Today* 12:860-869 (2007)). In contrast, multiplexed reporter screens such as we have described here are a powerful approach to identify ligands that specify a desired transcriptional output, or to identify and target therapeutically relevant receptor cross-talk pathways. Subsequent analysis using qPCR or microarrays can rapidly determine whether hits have bona fide impacts on receptor signaling.

II. Definitions

As used herein, "administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

As used herein, the term "a combination of active agents" refers to a composition of at least two or more active agents.

As used herein, the term "counterion" refers to the ion that accompanies an ionic species in order to maintain electronic neutrality. Counterions can be atomic, such as fluoride, chloride, bromide, iodide, or metallic counterions. Counterions can also be molecular, such as acetate, succinate, maleate and embonate (pamoate). Counterions can be positively or negatively charged. Counterions of the present invention are negatively charged. In addition, counterions can have a charge greater than 1, such as 2 or more. One of skill in the art will appreciate that other counterions are useful in the present invention.

As used herein, the term "hydrate" refers to a compound that is complexed to at least one water molecule. The compounds of the present invention can be complexed with from 1 to 10 water molecules.

As used herein, the term "inhibiting" refers to a compound that partially or fully prohibits or a method of partially or fully prohibiting a specific action or function. "Activiating" refers to a compound that partially or fully enhances or allows or a method of partially or fully enhancing or allowing a specific action or function.

As used herein, the term "patient in need" refers to a patient suffering from diseases states related to inflammation, asthma, allergic reactions, inflammation, acute transplant rejection, graft v. host disease, and other immune-mediated diseases such as auto-immune disease, e.g., rheumatoid arthritis. Patients suffering from other conditions treatable with the compounds of the invention are also treatable with the methods of the present invention. Patients treatable using the methods of the present invention are animals such as mammals, including, but not limited to, primates (e.g., humans), cows, sheep, goats, horses, dogs, cats, rabbits, rats, mice and the like. In certain embodiments, the patient is a human. Additional diseases of interest include prostate cancer, hematologic malignancies such as lymphoma, breast cancer, headache syndromes (e.g. cluster headache), systemic and central nervous system vasculitides.

As used herein, the term "prodrug" refers to covalently bonded carriers which are capable of releasing the active agent of the methods of the present invention, when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of the active agents of the present invention include active agents wherein a hydroxy, amidino, guanidino, amino, carboxylic or a similar group is modified.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the basic compounds of the present invention are salts formed with acids, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the terms "treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

III. Method of Modulating a Glucocortocoid Receptor

The present invention provides a method of modulating a glucocorticoid receptor by administering to a patient in need of such treatment, a therapeutically effective amount of a compound described herein, e.g., Table 2.

Patients in need of such treatment often suffer from disease states related to inflammation, asthma, allergic reactions, inflammation, acute transplant rejection, graft v. host disease, and other immune-mediated diseases such as auto-immune disease, e.g., rheumatoid arthritis. Other disease states can be treated using the methods of the present invention.

IV. Administration

The compounds of the present invention can be administered as frequently as necessary, including hourly, daily, weekly or monthly. The compounds utilized in the pharmaceutical method of the invention are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch.

The pharmaceutical compositions can be administered to the patient in a variety of ways, including topically, parenterally, intravenously, intradermally, intramuscularly, intra-articularly, colonically, rectally or intraperitoneally. Preferably, the pharmaceutical compositions are administered parenterally, topically, intravenously, intramuscularly or orally.

In practicing the methods of the present invention, the pharmaceutical compositions can be used alone, or in combination with other therapeutic or diagnostic agents. The additional anticancer drugs used in the combination protocols of the present invention can be administered separately or one or more of the anticancer drugs used in the combination protocols can be administered together, such as in an admixture. Where one or more anticancer drug is administered separately, the timing and schedule of administration of each drug can vary. The other therapeutic or diagnostic agents can be administered at the same time as the compounds, separately or at different times.

In clinical studies, number of lesions, tumor size, and tumor growth rate can be monitored by radiography, tomography, and, where possible, direct measurement of tumor mass. Anti-tumor effects can also be measured using molecular biology and biochemistry techniques, such as ELISA, PCR, western blotting, or immunocytochemistry.

The pharmaceutically effective amount of a composition required as a dose will depend on the route of administration, the type of cancer being treated, and the physical characteristics of the patient. The dose can be tailored to achieve a desired effect, but will depend on such factors as body surface area, weight, diet, concurrent medication and other factors which those skilled in the medical arts will recognize.

The foregoing are general guidelines only that can be expanded or altered based on, for example, disease type and grade, patient age, health status, and sex, the particular drugs used in combination, the route and frequency of administration, and experimental and clinical findings using a multidrug combination.

V. EXAMPLES

Example 1

In Vitro Screening

Materials and Methods

Plasmids. mCherry and mOrange, cerulean, pENaC-luc, pFKBP5-luc and pGILZ-luc were donated. pSV40-RL is from Promega. Luciferase coding regions in pENaC-luc, pFKBP5-luc, pGILZ-luc, and pSV40-RL were replaced with various FPs using standard techniques. When necessary, site directed mutagenesis used the QuikChange mutagenesis kit and protocol (Promega).

Cell culture. Cell lines were grown in high glucose DMEM supplemented with glutamine, penicillin, streptomycin and 5% FBS (Hyclone).

Chemicals. A amanitin, Hpg, mitoxantrone, dex, DMSO, forskolin, rosolic acid, pararosaniline and ciclopirox olamine were from Sigma. Acl, doxorubicin, Emc, daunorubicin, marcellomycin, Cin B, and Cin A HCL were from the NCI/DTP Open Chemical Repository (http://dtp.nci.nih.gov).

Transfections. The day prior to transfection, ~3×10$^5$ cells were plated in 6-well dishes. Transfections used Lipofectamine 2000 (Invitrogen). 4 µg of total plasmid DNA were used for each transfection. For A549 cells, 500 µL of DNA/lipofectamine complex was added to 1.5 ml of DMEM with pen/strep and 5% FBS. For U2OS cells, 500 µl of DNA/lipofectamine complex was added to 1.5 ml of Optimem. After 3-4 hours of incubation, media was replaced with standard growth media.

Luciferase assays. Luciferase assays used the Promega Dual-Luciferase Reporter system. Briefly, cells were transfected with various firefly luciferase plasmids and pSV40-RL at a ratio of 10:1. The day after transfection, cells were split into 96-well dishes and treated with dex and various drugs. Cells were harvested in 50 µl 1XPLB (Promega) 12-18 hr after drug treatment and luciferase assays were performed on 10 µl of lysate. Luminscence was detected using an Ultra Evolution plate reader (Tecan).

Compound Screen. A549 cells were transfected with an equal mixture of pENaC-CFP, pGILZ-YFP, pFKBP5-OFP (1.3 µg each), or with pSV40-ChFP (4 µg). The next day, cells were mixed (~1.8×10$^4$ of the cells triple-transfected with pENaC-CFP, pGILZ-YFP, pFKBP5-OFP; ~2×10$^3$ cells transfected with pSV40-ChFP) and replated into 96 well plates (Costar 3603). 2 hours later, library compounds (2.5 µM) and dex (100 nM) were added using a Biomek robot. The following day, cells were fixed for 4 minutes in 4% paraformaldehyde and fluorescence was measured sequentially for each reporter using a Safire plate reader (Tecan). Hits were scored based on the mean and standard deviation (s.d.) of the experimental wells on each plate. Criteria for a hit were if one reporter was more than 1.5×s.d. from the mean in duplicate, or if two reporters were more than 0.8×s.d. from the mean in duplicate. If the control SV40-ChFP was more than 2×s.d. from the mean in a single plate, or 0.8×s.d. in duplicate plates (in the same direction as the GR reporters), the well was not scored as a hit.

Quantitative PCR. Total RNA isolation used Trizol and Pure Link (Invitrogen). Random-primed cDNA was prepared from 1 µg of total RNA using MMLV-RT (Promega). 50 µg of resultant cDNA was used per 50 µl reaction containing 1.25 units of Taq DNA polymerase (Invitrogen), 1.5 mM MgCl$_2$, 300 nM of each primer (sequences available upon request), 0.15 mM dNTP mix, and 0.2×SYBR green dye (Molecular Probes) in 1×PCR buffer (Qiagen). Real-time PCR used an Applied Biosystems 7700 machine and was analyzed by using the δδCt method (Applied Biosystems Prism 7700 Users Bulletin No. 2). Rpl19 expression was used for data normalization. Relative message levels between samples were compared using non-parametric rank-sum tests. Data from representative experiments are shown; qualitatively similar data were obtained in replicate experiments.

TABLE 1

Number of reporters scored as hits

|  | Total | 1 reporter | 2 reporters | 3 reporters |
|---|---|---|---|---|
| Primary Hits | 66 | 20 | 34 | 12 |
| Known NR ligands | 14 | 6 | 5 | 3 |
| Other | 52 | 14 | 29 | 9 |

TABLE 2

Screen data for selected compounds

|  | ENaC-CFP | GILZ-YFP | FKBP5-OFP | Dose dependent[a] |
|---|---|---|---|---|
| Aclacinomycin | ↓↓↓[b] | ↓↓↓ | ↓↓↓ | yes |
| Ciclopirox olamine | ↓[c] | ↓ | no effect | yes |
| Ellagic Acid | No effect | ↓ | ↓ | no |
| Erythromycin estolate | No effect | ↑[d] | ↑ | no |
| Forskolin | No effect | ↑ | No effect | yes |
| Hpg. caproate | No effect | ↓↓↓ | ↓↓↓ | yes |
| Mepenzolate | No effect | ↓ | ↓ | no |
| Mitoxantrone | ↓↓↓ | ↓↓↓ | ↓↓↓ | yes |
| Pararosaniline | ↓ | ↓ | No effect | yes |
| Reserpine | ↑ | ↑ | ↑ | no |
| Rosolic Acid | ↓ | No effect | ↓ | yes |
| Thiamphenicol | No effect | No effect | ↑↑↑[e] | no |

[a]indicates whether the drug acted dose-dependently on GR-luciferase reporters
[b]more than 2 standard deviations (s.d.) less than the mean (↓↓↓)
[c]0.8 to 2 s.d. less than the mean (↓);
[d]0.8 to 2 s.d. greater than the mean (↑)
[e]more than 2 s.d. greater than the mean (↑↑↑)
*Hydroxyprogesterone caproate Results
Simultaneous Measurement of GR Response at Four Promoters To measure GR regulation of multiple promoters simultaneously, we used fluorescent proteins (FPs) with different excitation/emission properties (Shaner, N.C. et al., *Nat Methods* 2:905-9 (2005)) in combination with regulatory elements for ENaC, GILZ, and FKBP5 (Mick, V. E. et al., *Mol Endocrinol* 15:575-588 (2001); Hubler, T. R. et al., *Cell Stress Chaperones* 9:243-52 (2004)), three genes strongly induced by GR (Rogatsky, I. et al., *Proc Natl Acad Sci USA* 100: 13845-50 (2003); Wang, J. C. et al., *Proc Natl Acad Sci USA* 101:15603-8 (2004)) and believed to be clinically relevant GR targets (Woodruff, P. G. et al., *Proc Natl Acad Sci USA* 104:15858-63 (2007); Ayroldi, E. et al., *J Clin Invest* 117: 1605-15 (2007); Wang, H. C. et al., *J Biol Chem* 275:8600-9 (2000)). We linked GR-responsive regulatory regions for these genes to cDNAs encoding cerulean fluorescent protein (CFP), yellow fluorescent protein (YFP) and mOrange fluorescent protein (OFP). The FP-reporter constructs (pENaC-CFP, pGILZ-YFP, and pFKBP5-OFP) were transfected individually into A549 cells, a model of GR signaling. Transfected cells exhibited visible induction of fluorescence after exposure to dexamethasone (dex), a synthetic GR ligand (FIG. 1A, B).

We and others have previously used monochrometer-based fluorescence plate readers to quantify the expression of fluorescent proteins within cultured cells (Richards, B. et al., *Cytometry* 48:106-12 (2002); Pollitt, S. K. et al., *Neuron* 40:685-94 (2003)). We applied this system to measure dex-induced fluorescence from each of the GR-responsive reporters. We readily detected increases in peak fluorescence in A549 cells transfected with the pENaC-CFP, pFKBP5-OFP, and pGILZ-YFP reporters (FIG. 1C). In contrast, a constitutive SV40-mCherry (pSV40-mCh) fluorescent protein reporter did not respond to dex (FIG. 1C).

Figure 1:
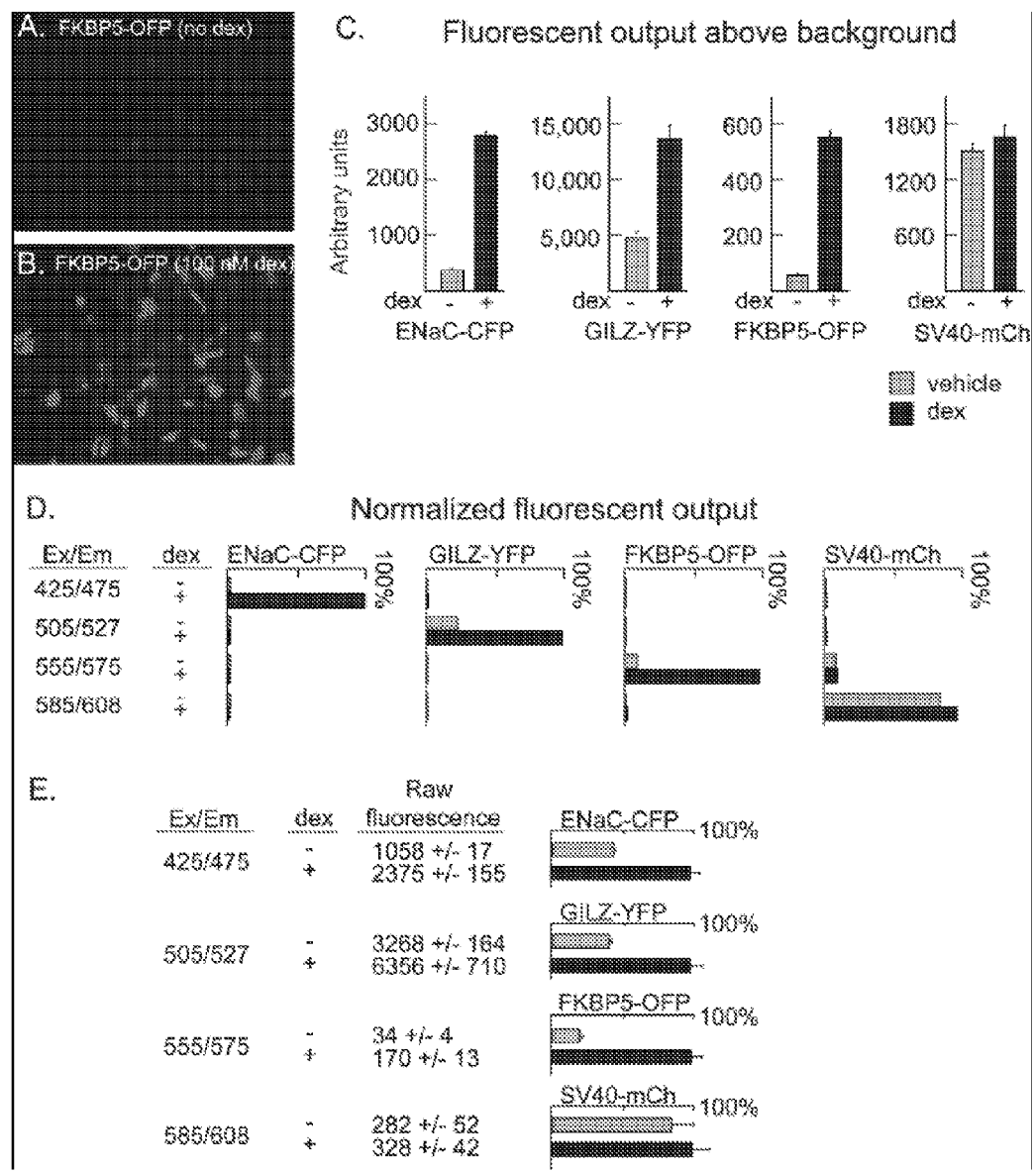
FIG. 1 shows measurement of activity from four promoters simultaneously with fluorescent reporters.

For simultaneous measurement of four reporters, we defined four excitation/emission parameters in which each FP variant was strongly detected at a single setting, with minimal or no activity detected with the other three settings (FIG. 1D). Only pSV40-mCh generated fluorescence output at more than one setting: fluorescence generated by pSV40-mCh with the excitation/emission pairing optimized for OFP (555/575, FIG. 1D) was a small, constant percentage of the signal measured at the optimized mCh setting (585/608, FIG. 1D). This did not significantly alter the value of the OFP reporter. By transfecting all four reporters and sequentially measuring with the four optimized emission/excitation settings, we simultaneously measured the changes in transcription associated with GR activation from four promoters (FIG. 1E). Although co-transfecting the reporters lowered the level of fluorescent activity for each, the low standard deviations of the GR-inducible reporters relative to the level of activation (FIG. 1E) implied that each would clearly indicate GR activity in screens for GR modulators.

Example 2

Application of a Multi-Promoter Screen to Identify GR Modulators

We used the system of Example 1 to screen a library of 1040 natural products and FDA-approved drugs for modulators of GR signaling (Abbott, A. *Nature* 417:109). The screen design is outlined in FIG. 2. The pENaC-CFP, pGILZ-YFP, and pFKBP5-OFP reporters indicated GR signaling, while pSV40-mCh, an internal control, excluded non-specific transcription inhibitors and toxins. We screened the library in duplicate in the presence of saturating dex (100 nM). Z', a function that reflects the ability to discriminate between control and experimental wells (Zhang, J. H. et al., *J Biomol Screen* 4:67-73 (1999)), was determined for dex treatment of each GR reporter. The Z' values were: Z'(ENAC-CFP)=0.68; Z'(GILZ-YFP)=0.64; and Z'(FKBP5-OFP)=0.66. These indicate that the screen should efficiently identify compounds that increase or decrease fluorescence from any of the three experimental promoters (Zhang, J. H. et al., *J Biomol Screen* 4:67-73 (1999)).

In the primary screen, 66 compounds significantly (see Methods) modulated one, two, or three of the experimental reporters in duplicate plates. These primary hits included both general and promoter specific agonists and antagonists of GR activity. 14 were known NR ligands, comprising seven glucocorticoids, two anti-androgens, three estrogens, and two progesterones. Of the hits not known to be NR ligands, secondary assays using newly purchased compounds yielded eleven molecules whose effects repeated, six of which dose-dependently altered GR signaling in luciferase assays (Table 1, 2). Further analyses of selected compounds are described below.

Example 3

Identification of Other GR Antagonists

Anthracyclines are GR Antagonists

Aclacinomycin (Acl), an anthracycline anti-neoplastic antibiotic, and mitoxantrone, a closely related anthracenedione, were non-selective GR antagonists in the primary screen (Table 2) and validated as antagonists of GR in A549 cells in luciferase assays (FIG. 3A). Both also inhibited GR in U2OS-GR cells (FIG. 3A), which is a bone sarcoma cell line used to study GR signaling (Rogatsky, I. et al., *Proc Natl Acad Sci USA* 100:13845-50 (2003)).

To investigate structure activity relationships, we tested the effects of several additional anthracyclines on GR signaling using luciferase assays. Anthracyclines contain a tetracyclic aglycone core attached to at least one sugar residue (e.g. Acl, FIG. 3B) and intercalate GC sequences within DNA. Cinerubin (Cin) B and Cin A HCl, which both contain a trisaccharide chain attached to the aglycone moiety and are very similar to Acl (FIG. 3C, compare to 3B), potently inhibited GR activity (FIG. 3C). In contrast, marcellomycin, also a trisaccharide anthracycline, had no impact on GR-mediated induction of the reporter. Notably, marcellomycin shares an identical aglycone to Cin B, but has slight differences in the trisaccharide chain (FIG. 3C). Doxorubicin and daunorubicin, which are monosaccharide anthracyclines, inhibited GR, although they were more than 10-fold less potent than Acl and Cin B. Similar results were observed in U2OS-GR cells (not shown). Taken together, these results show that the sugar moieties attached to the aglycone core affect the transcription of GR-regulated genes.

To test whether these effects were solely attributable to non-specific inhibition of RNA polymerase II (Pol II), we compared the effects of α amanitin, a direct inhibitor of Pol II, to Acl (FIG. 3D). Both drugs were tested on a GR-dependent and a GR-independent reporter (FIG. 3D). As expected, α amanitin reduced the activity of both reporters to similar extents. In comparison, treatment with Acl reduced GR activation of pENaC-luc much more than the constitutive reporter, pSV40-rl. Thus Acl, and likely the other anthracyclines we tested, do not inhibit GR solely through non-specific blockade of Pol II.

To test whether the plasmid-based results predict regulation of native promoters, we used qPCR to measure the effects of two of the most potent anthracylines, Cin B and Acl, on several endogenous GR target genes. Expression of ribosomal protein L19 (RPL19), which does not respond to GR, was the reference standard. Both drugs inhibited GR at the tested promoters (FIG. 3E). Certain anthracyclines thus are potent, non-selective GR antagonists. Moreover, the plasmid based screening system identifies chemicals that act at endogenous GR genes within native chromatin.

Selective GR Antagonists

Ciclopirox olamine, rosolic acid, and pararosaniline, not previously known to modulate GR signaling, were each identified in the primary screen as selective GR antagonists. The steroid hormone hydroxyprogesterone caproate (Hpg), a progestin, also had strong selective effects in the primary screen (Table 2). We determined that all four compounds exhibited dose dependent effects on GR-mediated activation in luciferase assays (FIG. 4A), suggesting drug-like activities for each. We next tested whether the effects on the FP reporters predicted regulation of endogenous genes. qPCR showed that all four compounds affected the expression of endogenous GR target genes (FIG. 4B), establishing these compounds as bone fide GR modulators. Ciclopirox olamine was a general GR antagonist, whereas Hpg, rosolic acid and pararosaniline selectively modulated endogenous GR target genes similarly to their regulation of the plasmid-based FP reporters (compare FIG. 4B to Table 2). Specifically, Hpg had no impact on induction of ENaC but reduced induction of GILZ and FKBP5, while rosolic acid inhibited GR induction of ENaC and FKBP5, but failed to inhibit GILZ (FIG. 4B). Pararosaniline also selectively inhibited the induction of endogenous ENaC transcription in comparison to FKBP5 (FIG. 4B). Taken together, these data show that selective modulation of GR signaling by compounds in the multiplexed plasmid screen predicts selective effects on endogenous gene transcription.

Both rosolic acid and pararosaniline have similar structures consisting of a single carbon linked to three phenyl groups. To establish further a structure activity relationship, we tested two additional compounds with related structures, NSC55861 and NSC636788. NSC55861 has a central carbon, attached to three phenyl groups; NSC636788 maintains a central carbon, but has more divergent side chains (FIG. 4C). Both compounds dose dependently reduced GR activity on the luciferase reporter (FIG. 4C), establishing this group of related chemicals as a novel class of GR modulators.

Example 4

Cell-Selective Modulation of GR Target Genes

Erythromycin estolate was a potential GR modulator in the primary screen, but did not exhibit dose dependent effects on GR-inducible luciferase reporters in secondary screens (Table 2). However, since erythromycins have been implicated in immunomodulation (Rubin, B. K. Am *J Med* 117 Suppl 9A, 2S-4S (2004)), we tested whether other macrolide antibiotics would exhibit more robust effects on GR target promoters. We discovered that an esterified derivative of erythromycin, erythromycin cyclopentylpropionate (Emc), modestly increased dex-induced activation of the pENaC-luc reporter in A549 cells, whereas in U2OS-GR cells, Emc strongly activated pENaC-luc, even in the absence of dex (FIG. 5A). Saturating amounts of dex overcame the effect in U2OS-GR cells, suggesting mechanistic overlap between the Emc target and GR on gene transcription (e.g. competition for a shared co-factor). Similar results were seen with a second transfected reporter, pGILZ-luc (FIG. 5A). Thus, Emc modulates GR activity, and, in contrast to the other GR modulators we identified, the effect of Emc on GR-mediated reporter activation differed between A549 and U2OS-GR cells.

We used qPCR to confirm this finding with respect to the transcription of endogenous GR target genes. As predicted, Emc activated endogenous GR target genes in the absence of dex in U2OS-GR cells (FIG. 5B), whereas in A549 cells, combined treatment with dex and Emc augmented endogenous gene transcription above treatment with either agent alone. Thus, Emc modulates the expression of endogenous GR target genes, and cell-specific factors influence this activity.

Example 5

Cross-Talk Mediated Modulation of GR

Forskolin was a GR agonist in the primary screen (Table 2). Previous reports have shown that forskolin increases the expression of GR-dependent reporters through cross-talk with cAMP signaling pathways (Seamon, K. B. et al., *J Cyclic Nucleotide Res* 7:201-24 (1981); Imai, E. et al., *J Biol Chem* 268:5353-6 (1993)). We confirmed that forskolin increases GR activity using luciferase assays in A549 and U2OS-GR cells (FIG. 5C). Next, we used qPCR to assess the impact of forskolin on the transcription of endogenous GR target genes. Forskolin modestly increased the dex-induced expression of three GR target genes; the increase in FKBP5 transcripts was significant (FIG. 5D). Thus, the screening system has sufficient sensitivity to identify compounds that augment GR activity at endogenous genes via heterologous pathways, and therefore provides a system for discovering non-ligand potentiators of GR signaling.

Example 6

In vivo Screening

Mice were injected with 7.5 mg/kg aclacinomycin. One hour later, mice were injected with 2.5 mg/kg dexamethasone. After 6 hours, lungs, liver, heart and skeletal muscle were harvested for RNA preparation. qPCR was performed on isolated RNA from these tissues to analyze expression levels of various genes that are regulated by glucocorticoids. Aclacinomycin blocked the activation of various genes such as KLF15 and FKBP5 by dexamethasone, but did not inhibit repression of the cytokine CCL2 by dexamethasone (see FIGS. 6-9).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of selectively modulating transcriptional regulation by a glucocorticoid receptor, the method comprising the step of: administering to a patient in need thereof, a therapeutically effective amount of aclacinomycin and a glucocorticoid compound, thereby blocking the activation of genes induced by the glucocorticoid compound without inhibiting the repression of genes by the glucocorticoid compound, wherein the glucocorticoid compound is dexamethasone, and wherein the method of modulating ameliorates a disease selected from the group consisting of: asthma, rheumatoid arthritis, hematologic malignancy, prostate cancer, and breast cancer.

2. The method of claim 1, wherein the administration is via topical, oral, intravenous, intradermal, intramuscular or parenteral administration.

3. The method of claim 1, wherein aclacinomycin and the glucocorticoid compound are administered separately.

4. The method of claim 1, wherein aclacinomycin and the glucocorticoid compound are admixed.

5. The method of claim 1, wherein aclacinomycin and the glucocorticoid compound are administered at the same time.

6. The method claim 1, wherein aclacinomycin and the glucocorticoid compound are administered at different times.

7. A method of ameliorating a disease comprising administering to a patient in need thereof a therapeutically effective amount of aclacinomycin and dexamethasone, wherein the disease is selected from the group consisting of: asthma, rheumatoid arthritis, hematologic malignancy, prostate cancer, and breast cancer.

* * * * *